United States Patent
Letot et al.

(10) Patent No.: US 6,506,215 B1
(45) Date of Patent: *Jan. 14, 2003

(54) SYNTHETIC KNEE SYSTEM

(76) Inventors: Patrick Letot, 1284 Hillgreen Dr., Los Angeles, CA (US) 90035; Patrick Bertranou, 1284 Hillgreen Dr., Los Angeles, CA (US) 90035

( * ) Notice: Subject to any disclaimer, the term of this patent is extended or adjusted under 35 U.S.C. 154(b) by 0 days.

This patent is subject to a terminal disclaimer.

(21) Appl. No.: 09/410,447

(22) Filed: Oct. 1, 1999

Related U.S. Application Data

(63) Continuation of application No. 09/075,813, filed on May 12, 1998, now Pat. No. 6,090,144.

(51) Int. Cl.[7] .................................................. A61F 2/38
(52) U.S. Cl. ............................... 623/20.29; 623/20.28; 623/20.15; 623/20.14
(58) Field of Search .................... 623/20.14, 20.15, 623/20.19, 20.21, 20.26, 20.27, 20.28, 20.29, 30.31, 20.33

(56) References Cited

U.S. PATENT DOCUMENTS

| | | | |
|---|---|---|---|
| 5,171,283 A | | 12/1992 | Pappas et al. |
| 5,387,240 A | * | 2/1995 | Pottenger et al. ........ 623/20.27 |
| 5,480,443 A | | 1/1996 | Elias |
| 5,549,684 A | | 8/1996 | Amino et al. |
| 5,609,639 A | * | 3/1997 | Walker ..................... 623/20.27 |
| 5,609,644 A | | 3/1997 | Ashby et al. |
| 5,755,801 A | * | 5/1998 | Walker et al. ........... 623/20.27 |
| 6,090,144 A | * | 7/2000 | Letot et al. .............. 623/20.27 |

FOREIGN PATENT DOCUMENTS

| | | |
|---|---|---|
| EP | 0 018364 B1 | 3/1979 |
| EP | 0 349 173 A1 | 6/1989 |
| EP | 0 568756 A1 | 7/1992 |
| EP | 0709073 A1 | 10/1995 |
| EP | 0716838 A2 | 11/1995 |
| EP | 0716 839 A1 | 12/1995 |
| EP | 0732091 A2 | 3/1996 |
| GB | 2061730 A | 10/1979 |
| GB | 2302282 A | 6/1995 |
| GB | 2304051 A | 6/1995 |
| WO | WO 94/13226 | 6/1994 |
| WO | WO 95/25484 | 9/1995 |
| WO | WO 95/27450 | 10/1995 |
| WO | WO 96/38103 | 12/1996 |

* cited by examiner

*Primary Examiner*—Corrine McDermott
*Assistant Examiner*—Alvin Stewart
(74) *Attorney, Agent, or Firm*—Blakely, Sokoloff, Taylor & Zafman LLP

(57) ABSTRACT

A knee prosthesis including a tibial component and a meniscal component adapted to be engaged through the tibial component through an asymmetrical engagement.

7 Claims, 5 Drawing Sheets

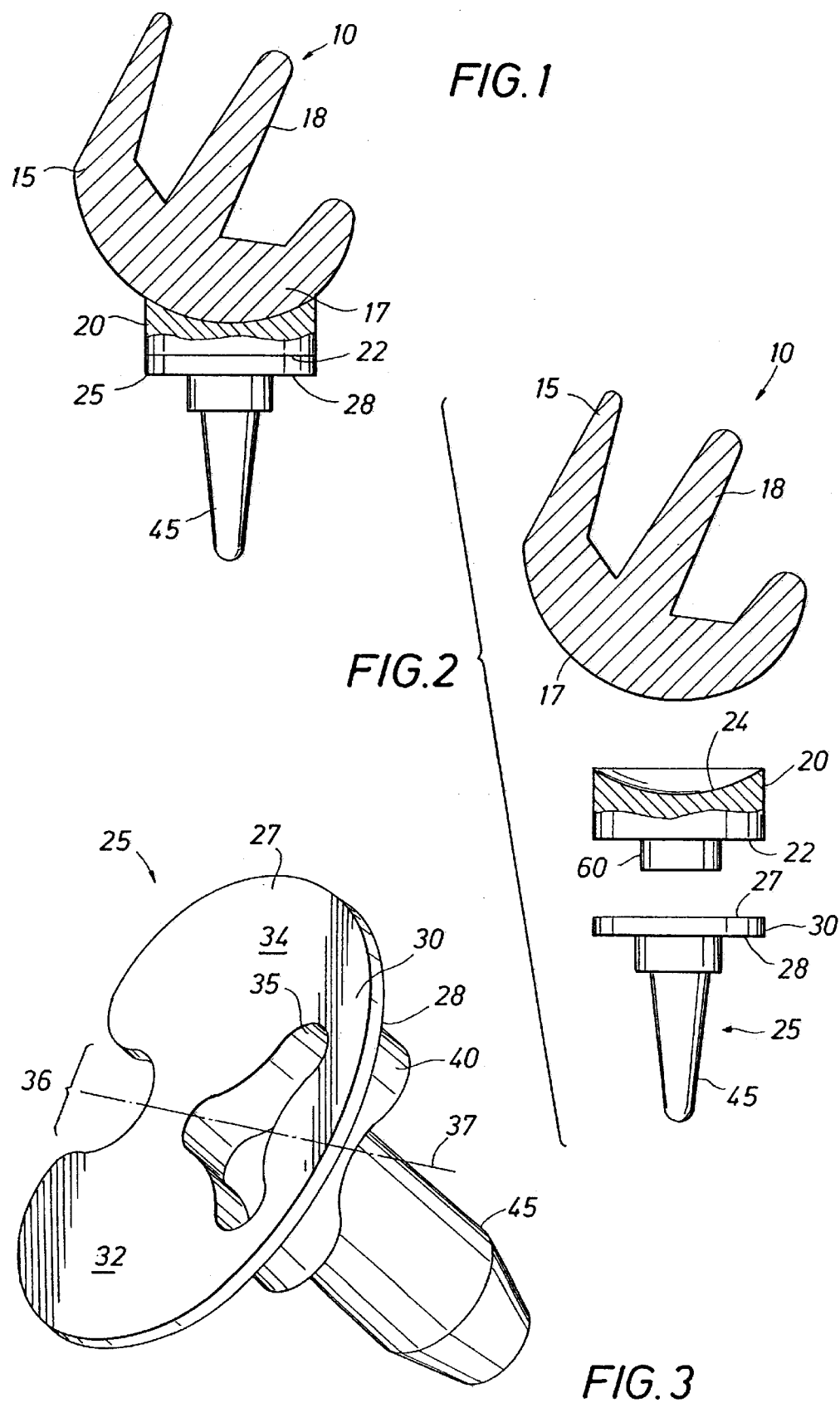

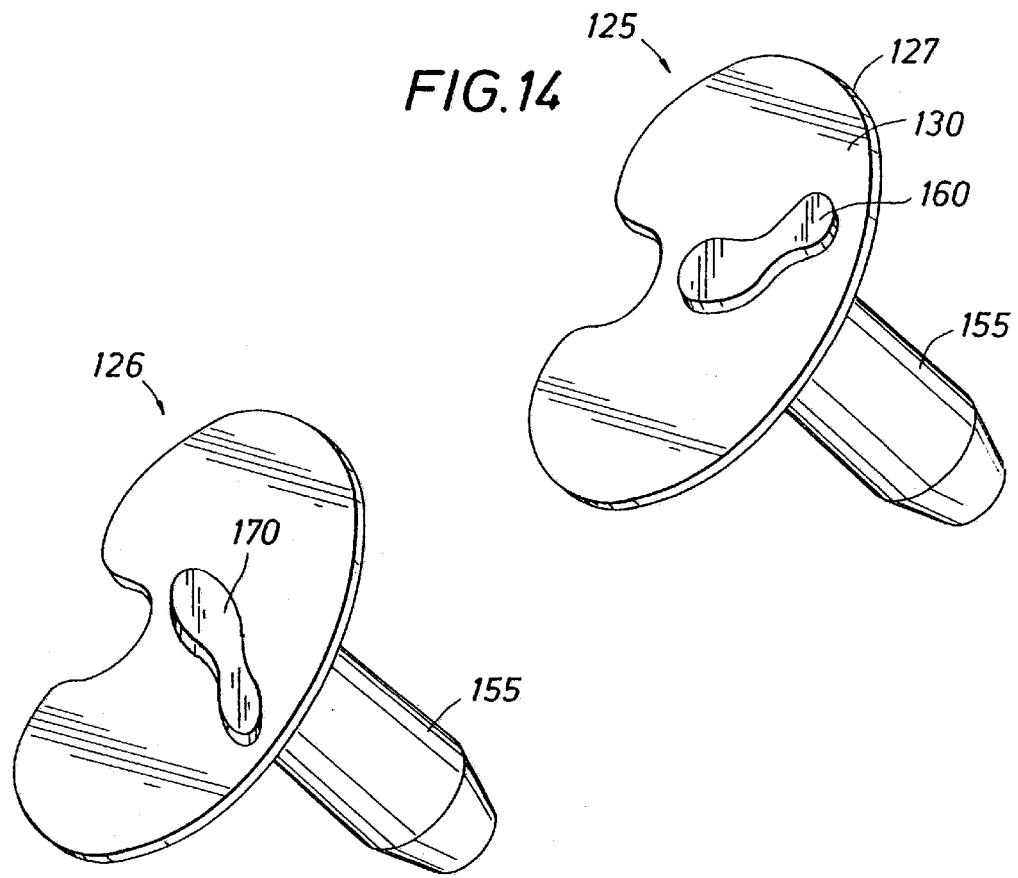
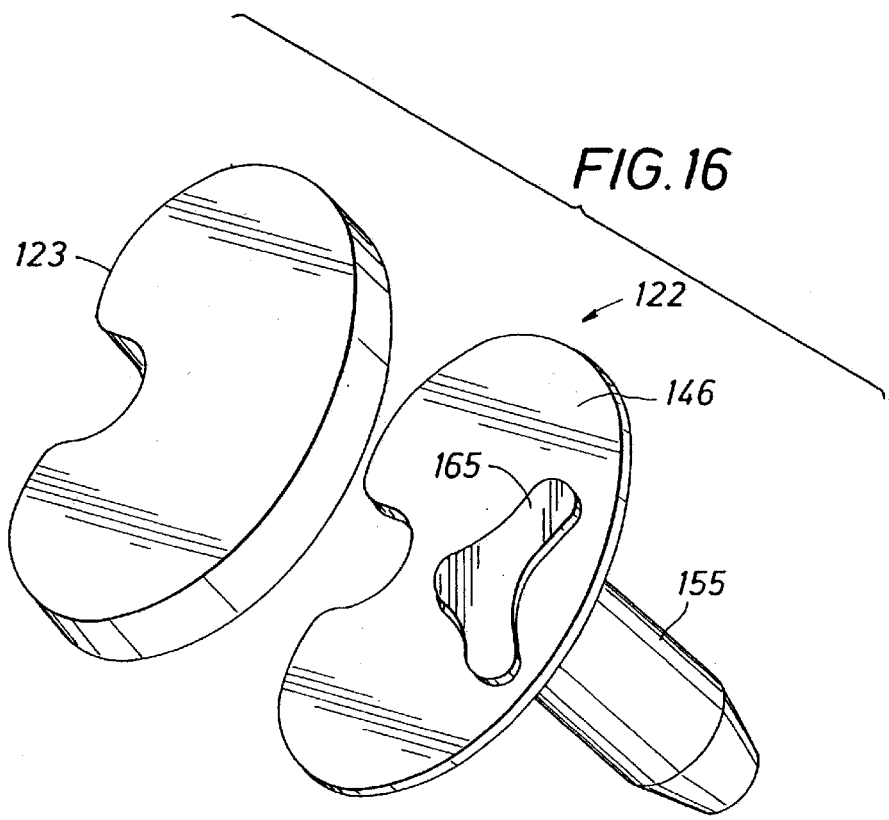

SYNTHETIC KNEE SYSTEM

RELATED APPLICATION

This application is a continuation of application Ser. No. 09/075,813, filed on May 12, 1998, now U.S. Pat. No. 6,090,144.

BACKGROUND OF THE INVENTION

1. Field of the Invention

The invention relates to a knee prosthesis.

2. Description of Related Art

The knee joint or articulation may be considered two condyloid joints, lateral and medial, between femur and tibia, and one arthrodial joint between the patella and the femur. The chief movements at the knee are flexion (decrease in the angle between two bones) and extension (increase in the angle between two bones) and rotation. These movements can be referred to as asymmetrical in that the movement of the left knee joint differs from the movement of the right knee joint. The individual displacement of the right and left knee joint during flexion and extension is also asymmetrical.

The knee joint combines a wide range of movement in one direction with a great weight-bearing capacity and considerable stability. The superior end of the tibia is the largest weight-bearing surface of the human skeleton. Its two articulating condyles or menisci are thickened and convex on their peripheral borders, and thin, concave, and free on their opposite borders. They are connected anteriorly and peripherally by transverse ligaments, and by part of the capsule of the knee joint, to the head of the tibia. These menisci lend some stability to the joint. Additional stability is given by the strong anterior and posterior cruciate ligaments which connect the tibia and femur inside of the joint and cross each other like the letter "X". The anterior cruciate ligament extends from the front of the intercondylar eminence of the tibia, upward and backward to the medial side of the lateral condyle of the femur. The posterior cruciate ligament extends from the posterior intercondylar fossa of the tibia, upward and forward to the lateral side of the medial condyle of the femur. The stability of the knee is secured by the muscles of the thigh, the joint capsule (system of tendons and ligaments that pass over the knee joint) and four ligaments—the two lateral ligaments and two cruciate ligaments.

Injuries to the knee are very common. The injuries often result to the menisci or the ligaments that hold them. Significant research and development in recent years has been directed to the development of knee prostheses that are reliable, i.e., prostheses that are not subject to unacceptable dislocation, not subject to bearing failure, not subject to loosening from the bones, and which provide a substantial duplication of the motion of the natural joint. In general, knee replacement prostheses are indicated for bi-cruciate retention application, unicondylar applications and for posterior cruciate retention applications. Other prostheses are indicated where neither posterior nor anterior cruciate ligaments are retained. The types of knee prostheses available can generally be classified as fixed prostheses and mobile prostheses.

Generally, either a fixed or mobile knee prosthesis involves a femoral component, a meniscal component, and a tibial component. The meniscal component generally is seated between the femoral component and the tibial component, each mated with the femur and tibia, respectively. The reference to either fixed or mobile prostheses generally concerns the meniscal component. In the fixed system, the meniscal component is fixedly attached to the femur or tibia. In the mobile system, prior art knee prostheses offer some limited range of symmetrical motion for each of the right and left knee joint prosthesis.

The fixed prosthesis is generally used on patients where there is severe damage to the femur and/or tibia around the knee joint or where neither the posterior or anterior cruciate ligaments of the knee joint cannot be retained. The fixed prosthesis generally does not allow any movement of the motion of the femur on the tibia, e.g., the "sliding-rolling" motion of the femur on the tibia. Instead, the meniscal component is fixed to the tibial component and/or the femoral component. This fixation generally includes screw and bands. The fixed prosthesis also does not allow correction for a misplacement in rotation of the tibia component. Finally, the fixed prosthesis contributes to accelerated wear of the generally polyethylene meniscal component.

Mobile, i.e., sliding or moving, knee prostheses generally accommodate some movement by the meniscal component or the tibial component during knee joint movement. As noted above, the individual biomechanical displacement of the right and left knee joint during flexion and extension is asymmetrical. The natural meniscal displacement of a knee joint during extension, for example, is approximately 15 millimeter (mm) for the external (lateral) meniscus and 5 mm for the internal (medial) meniscus.

The general interest in the mobile prosthesis is to obtain a diminution of the constraint on the meniscal component by delivering a proper positioning of the meniscal component on the tibial component during and after movement. In most instances, the motions of prior art prostheses are limited to a simple rotation (flexion/extension) which is in some instances combined with anterior-posterior clearance. These protheses generally offer no lateral translation or anterior-posterior translation of the components, e.g., the meniscal component. The range of motion of the components for the displacement is limited generally because the guidance is accomplished on rails or the motion around a fixed axis. The existing mobile motions are also symmetrical and non-conforming to human biomechanical movements. For example, most mobile knee prostheses have an axis of rotation about which movements of flexion and extension take place[lace]. In these systems, the displacement of the meniscal component about the axis of rotation is symmetrical. For example, displacement of the external (lateral) portion of the meniscal component is equivalent to the displacement of the internal (medial) portion for extension and flexion. During flexion, this type of symmetrical displacement will cause the femoral component to strike and erode the internal meniscal component and reduce flexion.

Prior art mobile prostheses also offer no rotational misalignment correction, such as, for example, where the meniscal component is misaligned between the femoral and tibial components. This is especially true in those systems that provide guide rails in the seat of the tibial component for placement of the meniscal component. The mobile prostheses further provide a lack of simple transformation toward a fixed tibial plate in cases of lateral instability, risk of incorrect positioning, luxation of the meniscal component, and rupture of the posterior cruciate ligament. In this instance, additional surgery is necessary to place a fixed knee prosthesis.

The invention seeks to address the limitations inherent in prior art knee prostheses.

SUMMARY OF THE INVENTION

A fixed knee prosthesis and a mobile knee prosthesis are disclosed. The knee prosthesis includes a tibial component and a meniscal component adapted to be engaged to the tibial component in an asymmetrical manner. The mobile knee prosthesis of the invention is adapted for and addresses the biomechanical movements of a right and a left knee joint or articulation separately. In one embodiment, the tibial component of the knee prosthesis of the invention includes a tibial seat including a Y-shaped cavity having a first arm and a second arm intersecting at a base. The meniscal component includes a meniscal plate selectively configured about a sagittal plane for either a right or left knee and a protuberance extending from a bottom surface of the meniscal plate.

The protuberance of the meniscal plate has a shape adapted to conform in some measure with the base and one of the first arm and the second arm of the cavity of the tibial seat, according to whether the prosthesis is adapted for the right or left knee joint of the patient. In one embodiment, the engagement of the protuberance of the meniscal component with the cavity of the tibial component is such that the protuberance is free to move within a portion of the cavity in conformance with the biomechanical movements of a natural knee joint, e.g., larger displacement of exterior (lateral) meniscal component than the interior (medial) portion of the meniscal component. In this manner, the invention provides a knee prosthesis or system with asymmetrical movements that emulate the asymmetrical movements of natural biomechanics.

An alternative embodiment of the invention describes a meniscal component including a meniscal plate including a Y-shaped cavity having a first arm and a second arm intersecting at a base. In this embodiment, the tibial component includes a tibial seat and a protuberance extending from a top surface of the tibial seat. The protuberance of the tibial component has a shape adapted to conform in some measure with the base and either the first arm or the second arm of the cavity of the meniscal plate according to whether the replacement is for the right or left knee joint of the patient. Accordingly, in one embodiment, the protuberance of the tibial component and the shape of the meniscal component, particularly about a sagittal plane, is specific for a left or a right knee joint prosthesis. In one embodiment, the cavity of the meniscal component is adapted to move about the protuberance in the tibial component in accordance with the asymmetrical movements of natural biomechanics.

Additional features and benefits of the invention will become apparent from the detailed description, figures, and claims set forth below.

BRIEF DESCRIPTION OF THE DRAWINGS

FIG. 1 is a side sectional view of a knee prosthesis in accordance with an embodiment of the invention.

FIG. 2 is an exploded side sectional view of a knee prosthesis in accordance with an embodiment of the invention.

FIG. 3 is a top perspective view of the tibial component of the knee prosthesis with a Y-shaped cavity in accordance with an embodiment of the invention.

FIG. 14 is a top perspective view of the tibial component of a left knee prosthesis with a protuberance adapted to conform with a portion of the Y-shaped cavity of the meniscal component in accordance with a second embodiment of the invention.

FIG. 15 is a top perspective view of the tibial component of a right knee prosthesis with a protuberance adapted to conform with a portion of the Y-shaped cavity of the meniscal component in accordance with a second embodiment of the invention.

FIG. 16 is a top perspective view of the tibial component of a knee prosthesis with a Y-shaped protuberance adapted to conform with the Y-shaped cavity of the meniscal component in accordance with a second embodiment of the invention.

DETAILED DESCRIPTION OF THE INVENTION

Figure 4:
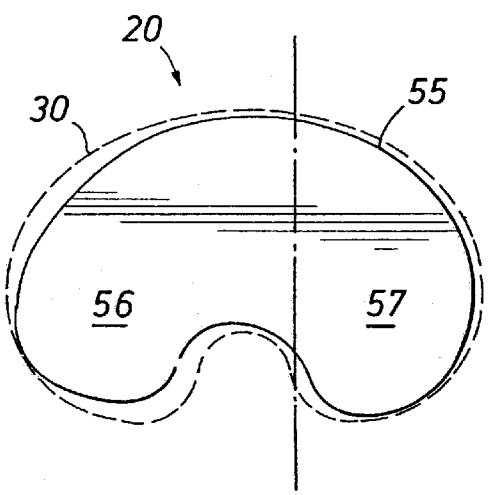
FIG. 4 is a top or superior side view of the left meniscal component of a knee prosthesis in accordance with an embodiment of the invention.

The invention relates to a knee prosthesis. The knee prosthesis provides three degrees of liberty in accordance with biomechanical movement data. An anterior-posterior translation is obtained as well as a median lateral motion. The knee prosthesis achieves these goals through the use of asymmetrical components specific for either the left or right knee. The invention is also designed to allow simple transformation, for example, from a mobile knee system to a fixed knee system.

FIG. 1 shows a side sectional view of a knee prosthesis according to an embodiment of the invention. FIG. 2 is an exploded view of the knee prosthesis of FIG. 1. Knee joint prosthesis 10 is functionally secured to a tibia and a femur of a human leg. Knee joint prosthesis 10 includes femoral component 15 that is rigidly connected to the superior end of a femur, generally after the femur has been resected in a manner that is well known in the art. Femoral component 15 includes a condylar portion 17 that contacts or engages meniscal component 20, which is more fully described below. Superiorly adjacent to condylar portion 17 on femoral component 15 is femoral stem 18 that acts as a fixing device to fix femoral component 15 to a femur.

In one embodiment, femoral component 15 is made of a biocompatible metal, such as, for example, titanium, titanium alloy, or cobalt-chromium alloy, or made of a biocompatible ceramic, such as, for example, alumina ceramic or zirconia ceramic. Femoral component 15 is fixed to a femur, for example, by cement or a hydroxyaptite coating on femoral stem 18. The hydroxyaptite coating is used in the instance to induce bone growth. It is to be appreciated that the femoral component is not required in the knee prosthesis of the invention. Instead, the meniscal component can be adjusted to conform and be compatible with the femur of the patient. However, to increase the longevity of the knee prosthesis and to avoid damage to the femur, femoral component 15 is generally recommended.

Meniscal component 20 is located between femoral component 15 and tibial component 25. The overall shape of meniscal component or plate 20 will be described in detail below, but here it is notable that meniscal component 20 has a generally planar inferior surface with protuberance (here labeled reference numeral 60) selectively chosen for the left or right knee, respectively, of a patient. In one embodiment, a superior surface of meniscal component or plate 20 has a generally condylar (concave) shape to match the opposing condylar (convex) surface of a femur or femoral component 15. In this manner, meniscal component 20 is able to articulate with condylar portion 17 of femoral component 15. The top surface of meniscal component 20 may also be configured to conform to prior art femoral components. In one embodiment, meniscal component 20 is made from biocompatible ultra-high molecular weight polyethylene (UHMWP) It is to be appreciated, however, that other suitable materials may be used consistent with the properties of biocompatibility and durability.

Meniscal component 20 is connected to tibial component 25 by inferiorly extending protuberance 60 that fits in a receiving cavity (not shown) of tibial component 25 depending upon whether knee prosthesis 10 is to be assembled in the left or right leg of a patient, respectively. Tibial component 25 is described in detail below, but here it is notable that tibial component 25 contains tibial seat 30 having a generally planar superior surface 27 to support the generally planar inferior surface 22 of meniscal component 20. Inferior surface 28 of tibial seat 30 contains inferiorly extending tibial keel 45 which is secured to the tibia of a patient.

In one embodiment, tibial component 25 is made of a biocompatible high-strength metal such as, for example, titanium, titanium alloy, or cobalt-chromium alloy or a biocompatible ceramic such as, for example, alumina ceramic or zirconia ceramic. Tibial component 25 is fixed to a tibia of a patient by, for example, making a hole in the tibia to support tibial keel 45 and cementing keel 45 to the tibia. In another embodiment, tibial component 25 is secured to the tibia of a patient by applying a hydroxyaptite coating on keel 45 to induce bone growth onto tibial component 25.

FIG. 3 shows an embodiment of tibial component 25 in accordance with the invention. Tibial component 25 includes tibial seat 30 having a generally planar superior surface 27. In one embodiment, the shape of tibial seat 30 resembles a painter's-pallet with an elliptic configuration incurvated or indented at one side. Indentation 36 defines tibial seat 30 with medial condylar portion 32 and lateral condylar portion 34. In this configuration, one skilled in the art will realize that the knee prosthesis of the invention can be affixed to a patient without the destruction of a viable posterior cruciate ligament. Indentation 36 between medial condylar portion 32 and lateral condylar portion 34 allows for posterior cruciate ligament retention.

The width of tibial seat 30 may be made to be specific for a patient. In one instance, for example, tibial seat 30 will have a standard thickness of, for example, approximately 5 millimeters (mm). In another instance, where more of a patient's tibia requires resection for placement of the knee prosthesis or system of the invention, tibial seat 30 may have a thickness of 10 mm or more. In the embodiment where the meniscal component is made of UHMWP, it is appreciated that conforming the meniscal components to the specifics of the patient's knee is much more cost effective than machining or casting a specific tibial component.

Tibial seat 30 has a substantially Y-shaped cavity 35 with a first arm and a second arm intersecting at a base. The base is proximally adjacent indentation 36 between medial condylar portion 32 and lateral condylar portion 34. In one embodiment, Y-shaped cavity 35 is formed with substantially arcuate surfaces and arcuate or softened edges throughout. In this embodiment, central axis 37 bisects cavity 35 between medial condylar portion 32 and lateral condylar portion 37.

Extending from inferior surface 28 of tibial seat 30 of tibial component 25 is keel 45. An upper portion 40 of keel 45 includes a cavity extending about and having the same shape as Y-shaped cavity 35 of tibial seat 30. In this manner, the opening through cavity 35 extends into upper portion 40 of keel 45. This extension of the Y-shaped cavity allows the stability and range of motion of the meniscal component to be adjusted, for example, by modifying the thickness or depth of protuberance 60—a deep or thick protuberance will be more stable and allow less meniscal component 20 motion, while a shallow or thin protuberance will be less stable but allow greater meniscal component 20 motion. In one embodiment, keel 45 is a fixed length such as, for example, approximately 12 mm. In another embodiment, keel 45 is modular and can be made of varying lengths.

FIGS. 4–7 show different views of meniscal components for a left and right knee prosthesis, respectively. FIG. 4 shows superior surface 55 of meniscal component 20 for a left knee prosthesis. Left meniscal component 20 has an asymmetrical shape similar to a painter's-pallet with an elliptic configuration incurvated or indented at one side. It is noted that the shape of left meniscal component 20, in this embodiment is not identical to the shape of tibial seat 30. The symmetrical shape of tibial seat 30 is presented in outline form beneath meniscal component 20 to demonstrate this difference. Similar to tibial seat 30, meniscal component has two condylar portions, medial condylar portion 56 and lateral condylar portion 57, to preserve a posterior collateral ligament. In one embodiment, superior surface 55 has concave condylar shapes to accommodate opposing convex condylar portions of femoral component 15. The shape of meniscal component 20 is chosen, in this embodiment to provide the closest duplication of human biomechanics by the movement of meniscal component 20 about cavity 35.

Figure 6:
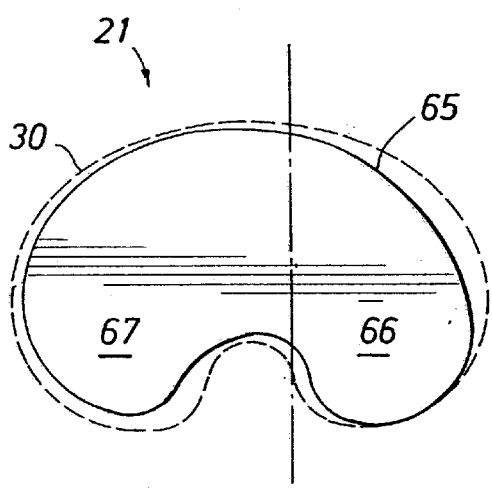
FIG. 6 is a top or superior side view of the right meniscal component of a knee prosthesis in accordance with an embodiment of the invention.

As shown in FIG. 6, right meniscal component 21 has an asymmetrical painter's-pallet (elliptical) shape to preserve a posterior collateral ligament. The shape is compared in the figure with the symmetrical shape of tibial seat 30. Meniscal component 21 includes medial condylar portion 66 and lateral condylar portion 67. In one embodiment, superior surface 65 of meniscal component 21 has concave condylar shapes to accommodate opposing convex condylar portions of femoral component 15.

Figure 5:
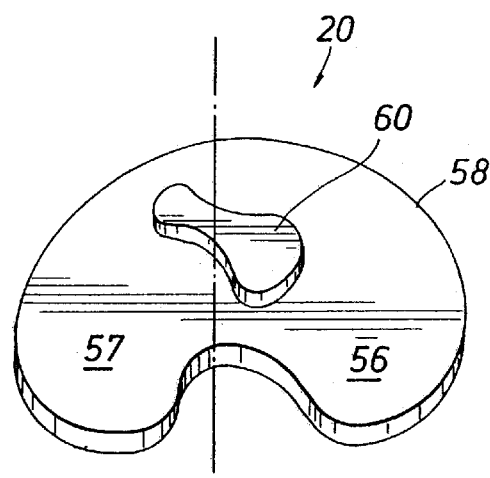
FIG. 5 is a bottom or inferior side view of the left meniscal component of a knee prosthesis with a protuberance adapted to conform with a portion of the Y-shaped cavity of the tibial component in accordance with an embodiment of the invention.
Figure 7:
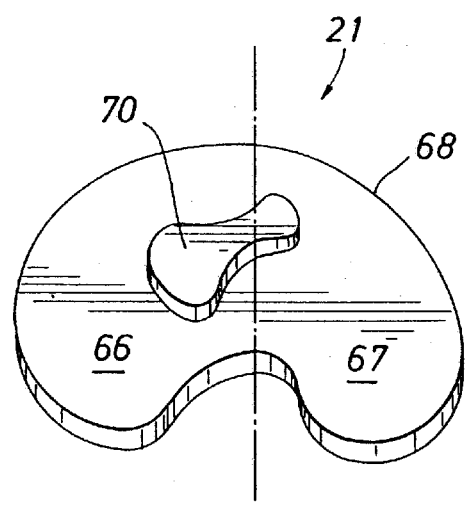
FIG. 7 is a bottom or inferior side view of the right meniscal component of a knee prosthesis with a protuberance adapted to conform with a portion of the Y-shaped cavity of the tibial component in accordance with an embodiment of the invention.

FIG. 5 shows an inferior view of left meniscal component 20. Inferior surface 58 is substantially planar to match substantially planar superior surface 27 of tibial seat 30. Inferior surface 58 includes protuberance 60 having a shape adapted to conform in part with the base and one arm of cavity 35 of tibial seat 30 but to allow some movement or play in this portion of the cavity. As shown in FIG. 7, inferior surface 68 of right meniscal component 21 similarly has a substantially planar surface and protuberance 70 adapted to conform in part with the base and the other arm of cavity 35 of tibial seat 30. In this manner, meniscal components 20 and 21 are specific for a left and a right knee of a patient, respectively.

Protuberances 60 and 70 have an asymmetrical shape with a mirror symmetry for the left and right meniscal components 20 and 21, respectively. The shape of protuberances 60 and 70 is of an asymmetrical bean form with a larger internal portion to mate with the base of Y-shaped cavity 35 of tibial component 25 and a smaller external portion to mate with an arm portion of Y-shaped cavity 35. The shape of protuberances 60 and 70 and the shape of meniscal components 20 and 21 shift the axis of displacement of meniscal component 20 or 21 on tibial seat 30 to a more medial or more lateral position, respectively. As noted, in this embodiment, protuberances 60 and 70 do not fit snugly in Y-shaped cavity 35 of tibial component 25, but instead are slightly smaller, particularly at their external ends, to allow movement of meniscal component 20 and 21 once the knee prosthesis is placed in the left or right leg of a patient, respectively. In one embodiment, protuberances 60 and 70 also have rounded edges to facilitate the movement of the protuberance in tibial cavity 35.

The asymmetrical shape of meniscal components 20 and 21 and protuberances 60 and 70, respectively, creates a controlled complex motion that includes a rotation combined with an anterior-posterior and a lateral translation. The range of motion duplicates the biomechanics of the human knee by privileging a larger displacement on the external portion of meniscal component 20 and 21 while limiting the displacement of the internal portion of meniscal component 20 and 21.

Figure 8:
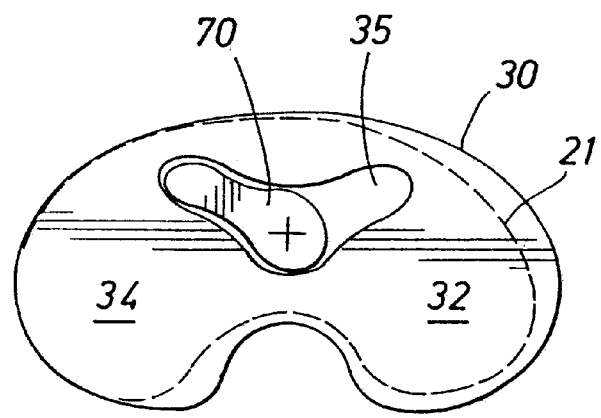
FIG. 8 is a top cross-sectional view of the right meniscal component of a knee prosthesis inserted into the Y-shaped cavity of the tibial component in a first position in accordance with an embodiment of the invention.
Figure 9:
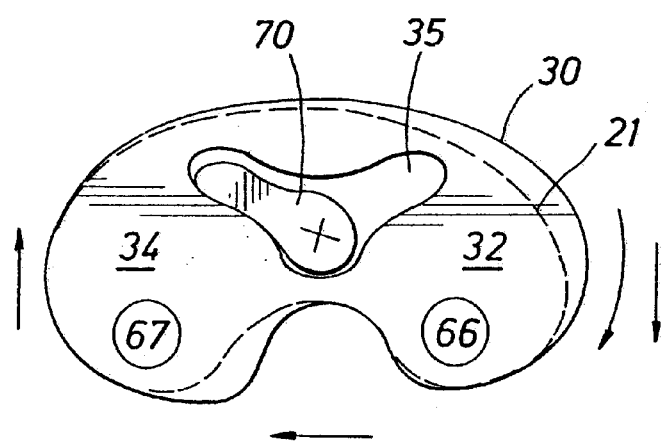
FIG. 9 is a top cross-sectional view of the right meniscal component of a knee prosthesis inserted into the Y-shaped cavity of the tibial component in a second position in accordance with an embodiment of the invention.
Figure 10:
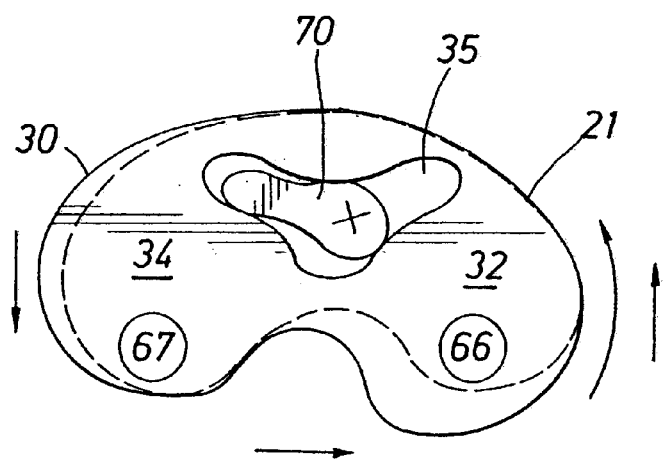
FIG. 10 is a top cross-sectional view of the right meniscal component of a knee prosthesis inserted into the Y-shaped cavity of the tibial component in a third position in accordance with an embodiment of the invention.

FIGS. 8–10 illustrate the controlled complex motion of right meniscal component 21 in tibial seat 30. Each of these figures present top or superior cross-sectional views of right meniscal component 21 seated in tibial seat 30. FIG. 8 illustrates a neutral position, FIG. 9 a flexion, and FIG. 10 an extension. Referring to FIG. 8, there is presented protuberance 70 mated with an arm portion and the base of cavity 35 of tibial seat 30. Bean-shaped protuberance 70 does not conform precisely to the dimensions of an arm and the base of cavity 35. Instead, protuberance 70 is able to move about a portion of cavity 35. The neutral position of FIG. 8 presents some point between flexion and extension.

As noted, FIG. 9 demonstrates the movement of meniscal component 21 after a flexion. The displacement of meniscal component 21 may be characterized as follows. Medial condylar portion 66 moves anteriorly along medial condylar portion 32 of tibial seat 30. Lateral condylar portion 67 of meniscal component 21 moves posteriorly about lateral condylar portion 34 of tibial seat 30. At the same time, meniscal component 21 rotates in a clockwise direction as illustrated in FIG. 9. There is also a medial translation.

FIG. 10 is directly opposite FIG. 9. FIG. 10 shows an extension having the following movements. Medial condylar portion 66 moves posteriorly along medial condylar portion 32 of tibial seat 30. Lateral condylar portion 67 of meniscal component 21 moves anteriorly about lateral condylar portion 34 of tibial seat 30. At the same time, meniscal component 21 rotates in a counter-clockwise direction as illustrated in FIG. 10. There is also a lateral translation.

The range of motion and the asymmetry of the motion of the knee prosthesis of the invention is created by the asymmetrical shape of meniscal component and 21 and the relationship of the symmetrical shape of cavity 35 of tibial seat 30 of tibial component 25 with the bean shape of protuberance 60 and 70 of left meniscal component 20 and right meniscal component 21, respectively. In the embodiment described, the asymmetrical shape of meniscal component 20 and 21 allows the external (lateral) portion (e.g., lateral condylar portion 66) to be displaced a greater distance than the internal (medial) portion (e.g., medial condylar portion 67). In one embodiment, for example, condylar portion 66 of meniscal component 21 may be displaced 14 mm while medial condylar portion 67 may be displaced 4 mm in the same flexion/extension displacement.

By placing either left meniscal component 20 or right meniscal component 21 on tibial component 25, protuberance 60 or 70, respectively, will be positioned in cavity 35 and have a range of controlled motion that will privilege an asymmetrical displacement of, for example, meniscal component 21 (lateral condylar portion 66 and medial condylar portion 67) on tibial component 25. It is to be appreciated that, in certain instances, the asymmetry described above with greater displacement privilege on, for example, lateral condylar portion 66 than medial condylar portion 67, can be reversed to obtain a larger displacement on the medial condylar portion and positioning the axis of displacement in a more lateral position on tibial plate 30.

Figure 11:
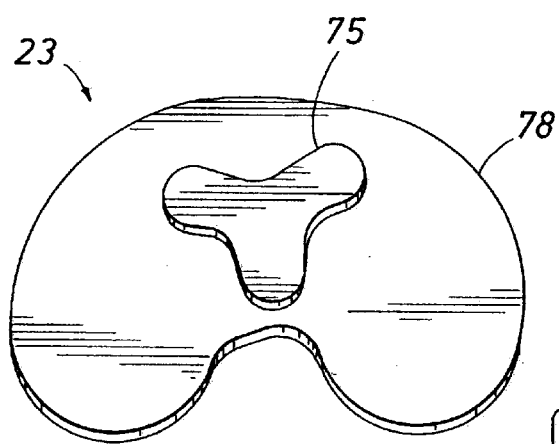
FIG. 11 is a top or superior side view of a meniscal component for a fixed knee prosthesis with a Y-shaped protuberance adapted to conform to the Y-shaped cavity of the tibial component in accordance with an embodiment of the invention.

In other instances, it may be necessary to limit the motion of the meniscal component. A surgeon may desire, for example, to place a fixed knee prosthesis or the patient's diagnois may require additional posterior stabilization, such as, for example, where the posterior cruciate ligament may not be retained. FIG. 11 shows an embodiment of the invention wherein meniscal component 23 is configured as a fixed insert. FIG. 11 shows the inferior side view of meniscal component 23. In this embodiment, meniscal component 23 has an elliptical shape similar to the shape of tibial seat 30 of tibial component 25, i.e., symmetrical. Extending from inferior surface 78 of meniscal component 23 is Y-shaped protuberance 75. Y-shaped protuberance 75 is symmetrical and complementary with Y-shaped cavity 35 of tibial seat 30 of tibial component 25. In one embodiment, Y-shaped protuberance 75 fits snugly in a conformal tibial cavity, such as tibial cavity 35 of tibial component 25 of FIG. 3.

The embodiment described with reference to FIG. 11 demonstrates an advantage of the configuration of the invention: the conversion, for example, from a mobile knee prosthesis or system to a fixed knee prosthesis or system does not require a new tibial component. Instead, the conversion is accomplished by replacing, for example, meniscal component 20 with meniscal component 23.

Figure 12:
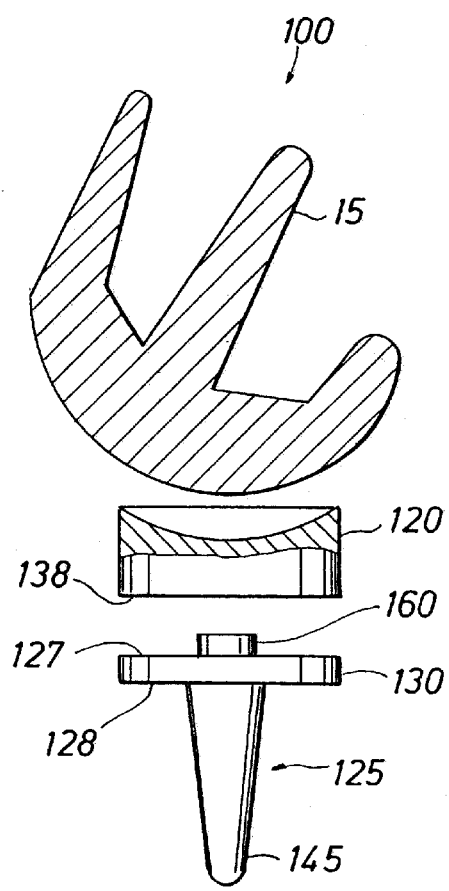
FIG. 12 is an exploded side sectional view of a knee prosthesis in accordance with a second embodiment of the invention.

FIGS. 12–15 show a knee prosthesis according to another embodiment of the invention. FIG. 12 is an exploded side sectional view of a knee prosthesis according to this embodiment. Knee prosthesis 100 includes femoral component 15 that is rigidly connected to the superior end of a femur as described above with respect to FIGS. 1 and 2 and the accompanying text. Meniscal component 120 is located between femoral component 15 and tibial component 125. Meniscal component 120 has a generally planar lower surface and, in one embodiment, a superior surface with a generally condylar (concave) shape to match the opposing condylar (convex) surface of a femur or femoral component 15. In one embodiment, meniscal component 20 is made from biocompatible UHMWP.

Meniscal component 120 is connected to tibial component 125 by a superiorly extending protuberance from tibial seat 130. The protuberance (labeled here as reference numeral 160) fits in a portion of a receiving cavity on the inferior side of meniscal component 120 depending upon whether knee prosthesis 100 is to be assembled in the left or right leg of the patient, respectively. Similar to the first embodiment, tibial component 125 includes tibial seat 130 having a generally planar superior surface 127. Tibial seat 130 resembles a painter's-pallet with an elliptic configuration incurvated or indented at one side. The indentation defines tibial seat 130 with two condylar portions. Extending from superior surface 127 of tibial seat 130 is protuberance 160, the orientation of which depends upon whether the knee prosthesis is for the left or right leg of a patient, respectively. It is to be noted here, unlike the first embodiment where meniscal component 20 was configured to be placed in one of a left or right knee prosthesis, respectively, in this embodiment, tibial component 125 is configured to be placed in either the left or right knee prosthesis, respectively. Alternatively, protuberance 160 may be modular and, thus, exchangeable allowing a single tibial component 125 for each of a right leg and a left leg and an individual protuberance selective for each articulation. Extending from inferior surface 128 of tibial seat 130 of tibial component 125 is keel 145 to affix tibial component 125 to a tibia.

Figure 13:
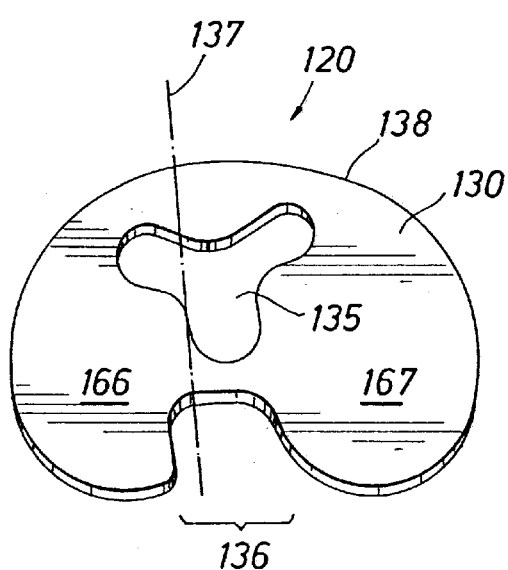
FIG. 13 is a bottom or inferior view of the meniscal component of a knee prosthesis with a Y-shaped cavity in accordance with a second embodiment of the invention.

FIG. 13 shows a view of inferior surface 138 of meniscal component 120. Meniscal component 120 resembles a painter's pallet with an elliptic configuration incurvated or indented at one side. The indentation defines two condylar portions: lateral condylar portion 166 and medial condylar portion 167. The shape of lateral condylar portion 166 and medial condylar portion 167 are not symmetrical in this embodiment. FIG. 13 is an embodiment of meniscal component 120 for a right knee prosthesis. In this instance, when viewed in a sagittal plane, lateral condylar portion 166 is slightly smaller or narrower than medial condylar portion 167 to allow more movement of lateral condylar portion 166.

In this embodiment shown in FIG. 13, inferior surface 138 of meniscal component 120 is generally planar with a substantially Y-shaped cavity 135 with a first arm portion and a second arm portion intersecting at a base. The base is proximally adjacent indentation 136 between the condylar portions of meniscal component 120. In this embodiment, axis of displacement 137 does not bisect cavity 135, but is slightly offset toward lateral condylar portion 166. It is to be appreciated that in some instances, it may be desirable to reverse the range of motion such that medial condylar portion 167 has a larger displacement. This may be accomplished by mirroring meniscal component 120 and shifting the axis of displacement for a right knee prosthesis.

FIGS. 14 and 15 shows top perspective views of embodiments of tibial components for a left and right knee prosthesis, respectively. Superior surface 127 of tibial seat 130 is substantially planar to match substantially planar superior surface 138 of meniscal component 120. In FIG. 14, superior surface 127 includes protuberance 160 having a shape adapted to conform in part with the base and an arm of cavity 135 of meniscal component 120. FIG. 14 is, for example, for a left knee prosthesis. FIG. 15 shows a similar tibial component having protuberance 170 extending from a superior surface of the tibial seat for a right knee prosthesis. In this manner, tibial components 125 and 126 are specific for a left and a right knee of a patient, respectively. Protuberances 160 and 170 have an asymmetrical shape with a mirror symmetry for the left and right tibial components, respectively. The shape of protuberances 160 and 170 is of an asymmetrical bean form with a larger internal portion to mate in part with the base of Y-shaped cavity 135 of meniscal component 120 and a smaller external portion. In this embodiment, protuberances 160 and 170 do not fit snugly in Y-shaped cavity 135 of meniscal component 120, but instead are slightly smaller, particularly at their external ends, to allow movement of meniscal component 120 once the knee prosthesis is placed in the left or right leg of a patient, respectively. In one embodiment, protuberances 160 and 170 have rounded edges to facilitate the movement of the protuberance in meniscal cavity 135.

The asymmetrical shape of meniscal component 120 and of the protuberances of tibial components 125 and 126 create a controlled complex motion that includes the rotation combined with an anterior-posterior and a lateral translation similar to that described above with reference to FIGS. 8–10 and the accompanying text. The significant difference is in the location of Y-shaped cavity (meniscal component) and protuberance (tibial seat). Once again, however, the range of motion duplicates the biomechanics of, for example, the human knee by privileging a larger displacement on the external (lateral) portion of meniscal component 120 while limiting the displacement of the internal (medial) portion of meniscal component 120.

FIG. 16 shows an embodiment of tibial component 122 that may be used in a fixed knee prosthesis configuration. Extending from the superior surface of tibial seat 146 of tibial component 122 is Y-shaped protuberance 165. Y-shaped protuberance 165 is symmetrical and complementary with a Y-shaped cavity of symmetrical meniscal component 123. In one embodiment, Y-shaped protuberance 165 fits snugly in the meniscal cavity.

It is to be appreciated that in the second embodiment, the height of the protuberance extending from the tibial seat is such that it sits within meniscal cavity 135 so that inferior surface 138 of meniscal component 120 contacts superior surface 127 of tibial seat 130. It is to be appreciated that meniscal component 120 may be made of different thicknesses to accommodate the proper placement and positioning of a knee prosthesis in a patient.

The use of the knee prosthesis of the invention can be used as a primary or revision knee system, for example, where a prior knee prosthesis failed. Further, the knee prosthesis of the invention allows a surgeon to make a decision during surgery whether to put a moving meniscal component or a fixed meniscal component into a knee prosthesis simply by choosing an appropriate meniscal component. Thus, the invention offers an asymmetrically designed knee prosthesis or system that in one sense mimics the biomechanical movements of a natural knee and in another is relatively easy to configure to an individual patient's needs.

The above embodiments described a Y-shaped cavity, protuberances that mate with a portion of the Y-shaped cavity, and asymmetric meniscal components. The invention is not to be interpreted as limited to any particular shape of meniscal component or cavity/protuberance. Instead, the invention recognizes the importance of an asymmetrical design, particularly in a mobile knee prosthesis or system (i.e., the asymmetrical design of the meniscal component relative to the tibial component or vice versa) commensurate with natural biomechanics. FIGS. 1–10 and 12–15 and the accompanying text presented various embodiments for a mobile knee prosthesis. The invention, however, recognizes that other designs based on the principles described herein are conceivable that capture this asymmetry and are therefore within the scope of the invention. Similarly, FIGS. 11 and 16 and the accompanying text presented various embodiments of a fixed knee system. These embodiments are particularly suitable for transformation from one of the mobile knee prostheses described herein. The invention recognizes that other designs based on the principles described herein are similarly conceivable and within the scope of the invention.

In summary, the preceding detailed description, described the invention with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A knee prosthesis comprising:

a tibial component having a cavity; and a meniscal component having a Y-shaped protuberance adapted for engagement to the tibial component through said cavity, said knee prosthesis adapted for only one of a right and a left knee joint of a patient.

2. The knee prosthesis of claim 1, wherein said cavity is a Y-shaped cavity and said meniscal component includes a plate to substantially engage a tibial seat of the tibial component, substantially all of the Y-shaped protuberance extending into the Y-shaped cavity.

3. The knee prosthesis of claim 2, wherein the tibial component further comprises a keel extending from a bottom surface of the tibial seat and adapted to be inserted into a tibia of a patient, a top portion of the keel formed about the cavity and having a keel corresponding to the shape of the cavity.

4. The knee prosthesis of claim 2, wherein the tibial seat has a substantially condylar shape with a medial condylar portion and a lateral condylar portion, the cavity disposed between the medial condylar portion and the lateral condylar portion such that a base of the cavity is in proximal relation to an opening between the medial condylar portion and the lateral condylar portion.

5. The knee prosthesis of claim 1, further comprising a femoral component adapted to be coupled to a base of a femur of a patient, and wherein the meniscal component is adapted to be located between the femoral component and the tibial component.

6. The knee prosthesis of claim 1, wherein the engagement is such that there is no predetermined axis of rotation.

7. The knee prosthesis of claim 1, wherein a dimension of the protuberance is less than a dimension of the cavity so that the protuberance is adapted to move within the cavity.

* * * * *